United States Patent
Klippenstein

[11] Patent Number: 5,868,713
[45] Date of Patent: Feb. 9, 1999

[54] PNEUMATIC RETRACTABLE SYRINGE

[75] Inventor: John Klippenstein, Kelowna, Canada

[73] Assignee: L.O.M. Laboratories Inc., Kelowna, Canada

[21] Appl. No.: 832,104

[22] Filed: Apr. 3, 1997

[51] Int. Cl.[6] .................................................. A61M 5/32
[52] U.S. Cl. ........................ 604/195; 604/198; 604/192; 604/187; 604/51; 604/70; 604/218; 604/232; 604/263; 604/110; 128/919
[58] Field of Search ..................... 604/195, 198, 604/192, 187, 51, 70, 218, 232, 263, 110; 128/919

[56] References Cited

U.S. PATENT DOCUMENTS

| | | |
|---|---|---|
| 5,120,310 | 6/1992 | Shaw . |
| 5,176,640 | 1/1993 | Nacci et al. . |
| 5,188,614 | 2/1993 | Hart . |
| 5,211,628 | 5/1993 | Marshall . |
| 5,224,936 | 7/1993 | Gallagher . |
| 5,334,155 | 8/1994 | Sobel . |
| 5,389,076 | 2/1995 | Shaw . |
| 5,407,436 | 4/1995 | Toft et al. ............................... 604/195 |
| 5,423,758 | 6/1995 | Shaw . |
| 5,433,712 | 7/1995 | Stiles et al. ............................. 604/195 |

FOREIGN PATENT DOCUMENTS

| | | |
|---|---|---|
| 0 479 217 | 4/1992 | European Pat. Off. . |
| 9000292 | 9/1991 | Netherlands . |
| WO 91 04760 | 4/1996 | WIPO . |

*Primary Examiner*—John D. Yasko
*Attorney, Agent, or Firm*—Robert H. Barrigar; Barrigar & Moss

[57] ABSTRACT

A pneumatic retractable syringe in which the needle is retracted into the barrel of the syringe following use by compressed gas that is released from a gas reservoir when the gas reservoir is ruptured by applying force to the plunger after injection is completed.

12 Claims, 2 Drawing Sheets

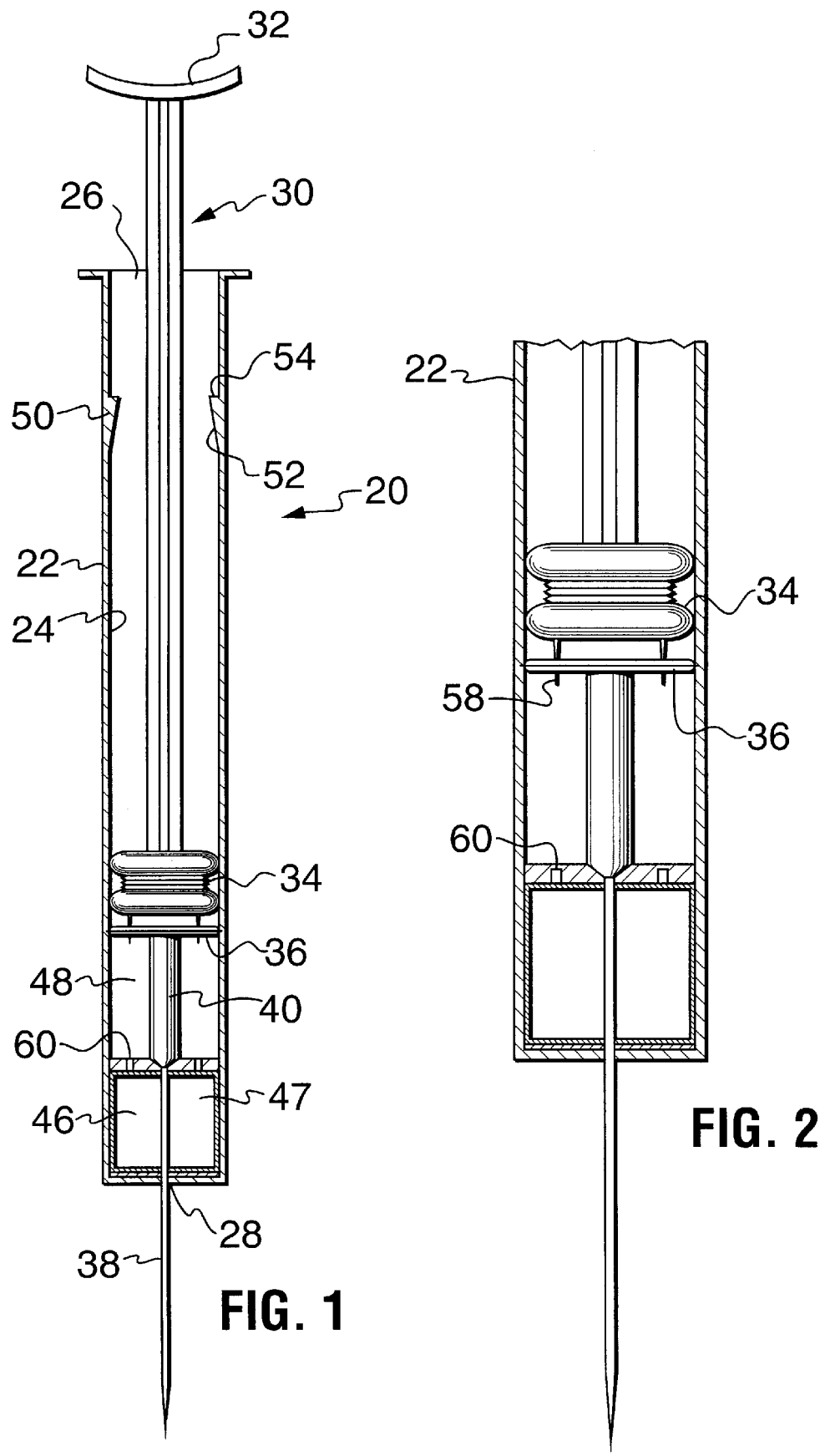

5,868,713

PNEUMATIC RETRACTABLE SYRINGE

FIELD OF THE INVENTION

The invention relates generally to a syringe in which the needle is retracted into the barrel of the syringe following use of the syringe, and more particularly to a syringe in which such retraction is effected by pneumatic means.

BACKGROUND OF THE INVENTION

It is well known that many communicable and dangerous diseases are spread through contacting the bodily fluids of an infected person. After use of a needle, residual bodily fluids are likely to remain on or within the needle. For this reason, syringes are typically intended for a single use only. In order to be handled safely after use, the needle of a syringe must be covered to prevent it from accidentally stabbing a person, thereby releasing residual bodily fluids into such person. Typically, a protective cap is provided with the syringe, which, after use of the syringe, can be used to cover the tip of the needle. However, it is common for medical personnel, when attempting to cap a used needle, to miss the cap and accidentally stab themselves, resulting in the potential exposure to communicable diseases.

There have been several attempts to address this problem by incorporating into syringes, mechanisms for retracting the needle into the syringe following use. However, these attempts have not, so far, provided a optimal solution to this problem. U.S. Pat. No. 5,334,155 discloses an evacuated double walled protective sheath. Before use, the partial vacuum within the protective sheath causes the sheath to fold inwardly upon itself so that the needle extends beyond the protective sheath and may be used for injections. Subsequent to injection, the double wall of the protective sheath can be breached in one place so that the inside of the protective sheath reaches atmospheric pressure. The protective sheath then extends to cover the projecting needle. However, the protective sheath may interfere with use of the syringe as it may obstruct the view of the point the needle is to be inserted into on the patient. In addition, it is inconvenient to use; after injection, the user must change the user's hand position on the syringe in order to breach the double wall and activate the sheath.

The protective safety device shown in U.S. Pat. No. 5,188,614 is a hollow cylindrical casing that encompasses the syringe. A dual component foaming agent is disposed at the downstream end of the casing. Following injection, the two components of the dual component foaming agent are mixed, creating an expanding foam mixture that forces the syringe back and encompasses the needle. However, this device suffers from the disadvantages that the casing may interfere with the use of the syringe in making injections as it changes the dimensions and size of the syringe significantly. In addition, a considerable amount of material is necessary in order to make the protective sheath, increasing the expense of both making and disposing of the device.

An optimal solution to the problem of how to prevent accidental needle stabbing after injection would include the following features: the mechanism should be simple in that it employs a minimal number of moving parts and is, accordingly, reliable in retracting the needle; syringes incorporating the mechanism should be inexpensive to manufacture; the mechanism should not increase significantly the waste plastic, or other materials, to be disposed of after use of the syringe; the mechanism should not change how the needle feels or is operated; and the mechanism should be simple to use. The pneumatic retraction mechanism of the present invention provides these features.

SUMMARY OF THE INVENTION

An object of one aspect of the present invention is to provide a syringe in which the needle is retracted into the barrel of the syringe following use.

In accordance with one aspect of the present invention there is provided a pneumatic safety syringe for reducing the risk of accidental needle stabbing after use. The pneumatic safety syringe comprises a barrel, a plunger, a needle header, a needle, a tube stop and a gas reservoir. The barrel has an inner surface, an upstream opening, and a downstream needle aperture. The plunger mates with the barrel and is mounted for axial movement within the barrel. The plunger has an upstream end that projects from the upstream opening of the barrel, and a plunger seal at the downstream end of the barrel. The plunger seal slidingly contacts the inner surface of the barrel in order to impede leakage of fluid past the plunger seal.

A needle header is mounted in the barrel downstream of the plunger seal. Before a medicament is injected using the syringe, the needle header is situated within the barrel such that the medicament is containable within the barrel downstream of the plunger seal and upstream of the needle header. A needle projects downstream from the needle header. The needle has an upstream intake for receiving the medicament into the needle. The upstream intake of the needle is attached to the needle header. The needle also has a downstream tip for releasing the medicament into a patient. The downstream tip of the needle projects out of the downstream needle aperture of the barrel before use of the syringe.

The needle header is releasably engaged to the barrel by a releasable holding means in order to resist axial sliding of the needle header within the barrel. The releasable holding means situates the needle header and the upstream intake of the needle within the barrel such that the downstream tip of the needle projects out of the downstream needle aperture of the barrel. The releasable holding means is released when a downstream post-injection force is exerted on the plunger and the plunger seal contacts the needle header, thereby overcoming the releasable holding means, permitting the needle header to slide axially within the barrel, and initially forcing the needle header downstream.

The barrel also contains a gas reservoir downstream of the needle header. The gas reservoir is ruptured by the needle header when the needle header is forced in a downstream direction after the releasable holding means is released. When the gas reservoir is ruptured, it releases a non-toxic compressed gas. The released non-toxic compressed gas is contained within the barrel in order to provide an upstream biassing pressure within the barrel upstream of the gas reservoir. The upstream biassing pressure biases the needle header to slide upstream.

In operation, when an injection force is applied to the plunger, the plunger seal imparts a downstream biassing pressure to the medicament contained in the barrel between the plunger seal and the needle. This downstream biassing pressure is sufficient to force the medicament through the upstream intake and into a patient via the downstream tip by the plunger. The releasable holding means resists the downstream biassing pressure exerted on the needle header by the medicament as the medicament is forced through the upstream intake. After substantially all of the medicament is forced into the needle, the plunger seal seals the needle intake. The downstream post-injection force exerted by the plunger overcomes the releasable holding means, thereby releasing the needle header to slide downstream. When the needle header ruptures the gas reservoir, the upstream biassing pressure of the released non-toxic compressed gas, biases the needle header to slide upstream within the barrel, thereby effecting withdrawal of the needle within the barrel.

BRIEF DESCRIPTION ON THE INVENTION

A detailed description of the preferred embodiments are provided herein below with reference to the following drawings in which FIG. 1, in a sectional view, illustrates a pneumatic retractable syringe in accordance with a preferred embodiment of the invention;

FIG. 2 is an enlarged sectional view of the pneumatic retractable syringe of FIG. 1; and, FIG. 3 is an enlarged sectional view of the needle header of the pneumatic retractable syringe of FIG. 1.

In the drawings, preferred embodiments of the invention are illustrated by way of example. It is to be expressly understood that the description and drawings are only for the purpose of understanding, and are not intended as a definition of the limits of the invention.

DETAILED DESCRIPTION ON THE INVENTION

Figure 3:
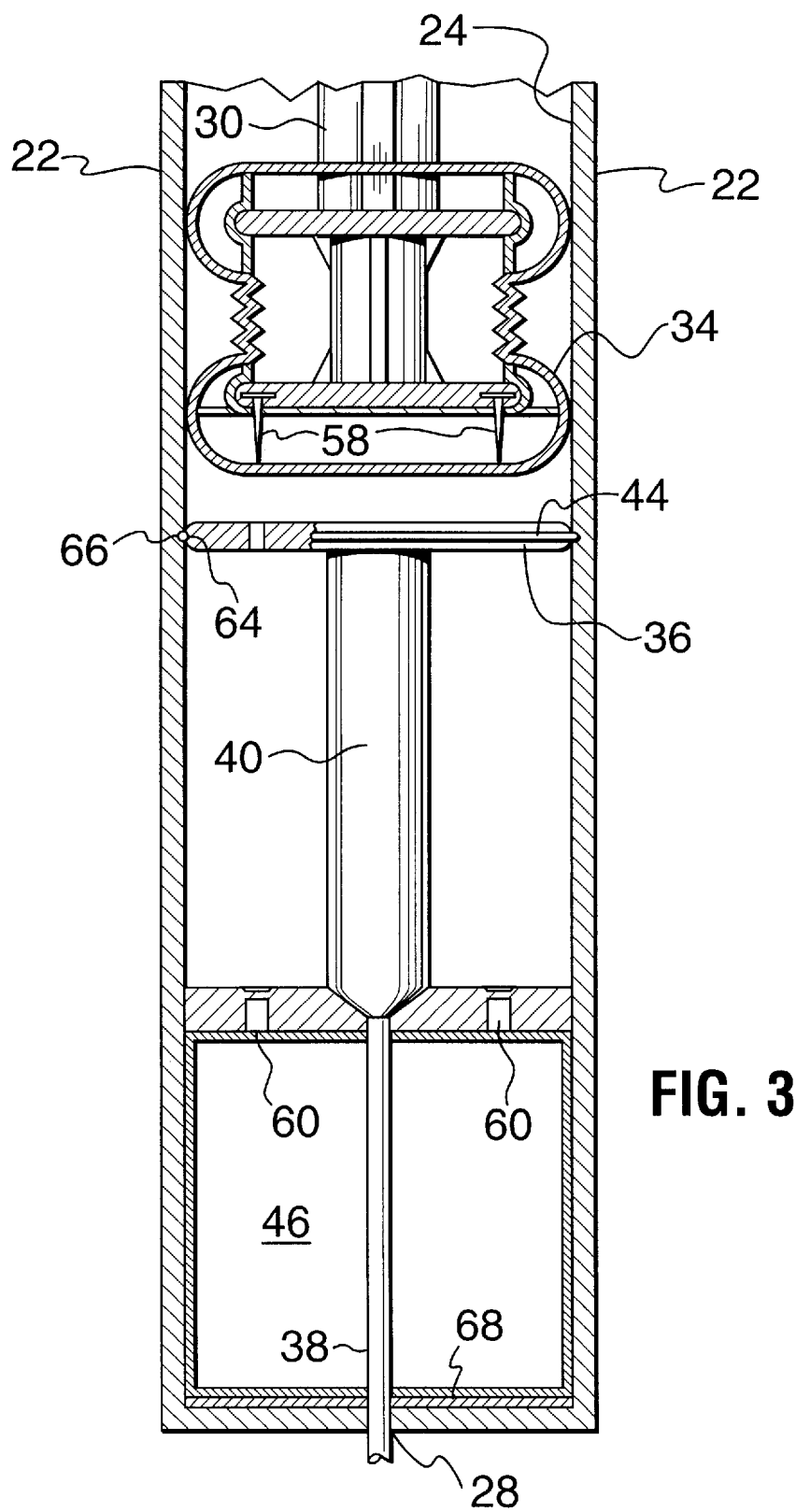

Referring to FIG. 1, there is illustrated in a sectional view, an pneumatic safety syringe 20 in accordance with a preferred embodiment of the invention. The syringe 20 includes a barrel 22 having an inner surface 24, an upstream opening 26 and a downstream needle aperture 28. A plunger 30 fits within the barrel 22 within a tolerance permitting the plunger 30 to slide within the barrel 22, while constraining the plunger 30 against rattling within the barrel 22 and providing some frictional resistance to longitudinal sliding of the plunger 30 within the barrel 22. The plunger 30 has an upstream end 32, preferably a thumb grip 32, and plunger seal 34 at a downstream end. The plunger seal 34 slidingly engages the inner surface 24 so as to impede leakage of fluid, whether air or a medicament 48, past the plunger seal 34 of the plunger 30.

Referring to FIG. 3, a needle header 36 is mounted in the barrel 22 downstream of the plunger seal 34 of the plunger 30. The needle header 36 secures the needle 38 in place within the barrel 22 such that a downstream tip 42 of the needle 38 projects out of the downstream needle aperture 28 of the barrel 22. The needle 38 has an upstream needle intake 40 which is attached to the needle header 36. The needle header 36 is secured to the inner surface 24 by a releasable holding means or tube stop 44 that resists sliding of the needle header 36 within the barrel 22. The releasable tube stop 44 can be overcome by a downstream post-injection force applied to the plunger 30, thereby causing the needle header 36 to slide axially downstream within the barrel 22. Preferably, the needle header 36 is generally disc-shaped and has an outer circular edge that touches the inner surface 24 of the barrel 22. In one embodiment, this outer circular edge has an inner concave recess 64, that is aligned with an outer concave recess 66 in the inner surface 24, to define a generally ring-shaped hollow. In such embodiment, the releasable tube stop 44 is an o-ring 44 located in the generally ring-shaped hollow. As there is insufficient room to accommodate the o-ring 44 in just one of the recesses, the o-ring 44 must be broken if the recesses are to slide past each other. Thus, for example, if the needle header 36 is forced downstream, the generally ring-shaped hollow will become smaller as it will be defined by the downstream part of the outer concave recess 66 and the upstream part of the inner concave recess 64 alone, and not by the entirety of both recesses. Thus, the o-ring 44 will become compressed between the downstream part of the outer concave recess 66 and the upstream part of the inner concave recess 64. The o-ring 44 resists this compression, thereby resisting misalignment of the inner concave recess 64 and outer concave recess 66 and axial sliding of the needle header 36. Preferably, the o-ring 44 will be sufficiently incompressible to resist fitting within one recess alone. Thus, in order to permit the recesses to slide past each other, sufficient force must be applied to overcome this resistance to compression or deformation of the o-ring 44.

A gas reservoir 46 is situated downstream of the needle header 36 within the barrel 22. By applying the downstream post-injection force on the plunger 30 to force the needle header 36 to slide axially downstream after all of the medicament 48 has been injected, the gas reservoir 46 can be ruptured, thereby releasing a non-toxic compressed gas 47. Preferably, the gas reservoir 46 is ruptured by a pair of spikes 58 that project downstream from the plunger seal 34. The pair of spikes 58 penetrate two aligned release valves 60 in the gas reservoir 46 when the needle header 36 is forced downstream by the plunger 30 after the o-ring 44 has been overcome by a downstream post-injection force exerted on and by the plunger 30. Preferably, the release valves 60 are weakened portions of the gas reservoir 46, and are more easily penetrated as a result.

In order to impede leakage of compressed gas 47 from the downstream needle aperture 28, a needle membrane 68 preferably surrounds the needle 38 where the needle 38 passes through the downstream needle aperture 28. The needle membrane 68 is fixed to the barrel 22 at and around the downstream needle aperture 28, and is tapered by preferably about 30 degrees where the needle membrane 68 contacts the needle 38. Once the needle 38 has been retracted, the needle membrane 68 will cover the downstream needle aperture 28 so as to impede the re-extension of the needle 38 through the downstream needle aperture 28.

In operation, after charging of the syringe 20 with the medicament 48 such that the barrel 22 contains the medicament 48 between the plunger seal 34 of the plunger 30 and the needle header 36, the medicament 48 is injected into a patient by applying an injection force to the plunger 30. Although, the medicament 48 while being injected is placed under pressure by the plunger 30 and therefore exerts a downstream pressure on the needle header 36, the resulting force on the needle header is not sufficient to overcome the o-ring 44. Thus, the o-ring 44 resists axial sliding within the barrel 22 while the medicament 48 is being injected. After substantially all of the medicament 48 has been injected, the plunger seal 34 of the plunger 30 seals the upstream intake 40 of the needle 38 and the downstream tip 42 of the needle 38 is withdrawn from the patient. Then a post-injection force is applied to the plunger 30; the post-injection force must be greater than the injection force as it must be sufficient to overcome the resistance to compression or deformation of the o-ring 44. Preferably the force required to overcome resistance to deformation of the o-ring 44 is in the order of 5 p.s.i.

The plunger seal 34 has a pair of spikes 58 projecting downstream. The spikes 58 are with the release valves 60 in the gas reservoir 46. As the needle header 36 is pushed downstream, the spikes 58 penetrate the release valves 60 thereby releasing the compressed gas 47. This released compressed gas 47 exerts an upwards biassing pressure on the needle header 36 and plunger 30 that forces both the needle header 36 and plunger 30 upstream, thereby retracting the needle 38 within the barrel 22.

As the downstream tip 42 of the needle 38 passes through the downstream needle aperture 28 of the barrel 22, the tapered portion of the needle membrane 68 flattens to cover the downstream needle aperture 28, thereby impeding re-extension of the needle 38.

The released compressed gas 47 forces the plunger 30 upstream such that the plunger seal 34 of the plunger 30 is forced upstream of a plunger lock 50. The plunger lock 50 impedes the plunger seal 34 of the plunger 30 from subsequently sliding downstream of the plunger lock 50. In the embodiment shown in FIG. 2, the plunger lock 50 has a downstream face that is shallow relative to the portion of the inner surface 24 surrounding the plunger lock 50 and a upstream face that is steep relative to the portion of the inner surface 24 surrounding the plunger lock 50. When the released compressed gas 47 forces the plunger 30 upstream, the plunger seal 34 of the plunger 30 is sufficiently compressible to enable the plunger seal 34 to ride over the shallow downstream face of the plunger lock 50. Once the plunger seal 34 is upstream of the plunger lock 50 the steep upstream face of the plunger lock 30 will impede subsequent downstream movement of the plunger 30.

Variations in what has been described and illustrated in this specification will readily occur to those skilled in the technology. For example, breakable tabs could replace the o-ring 44. Instead of being penetrated by the spikes 58, the gas reservoir 46 could be broken by being crushed by the needle header 36 or being torn away from the inner surface 24, thereby being torn open by the downstream movement of the needle header 36. In another embodiment, a flotation gasket is mounted for axial sliding within the barrel 22, and is located downstream of the needle header 36. The spikes 58 can project through the flotation gasket to rupture the gas reservoir 46. The flotation gasket has a symmetrical configuration so as to evenly force the needle header 36 upstream, thereby helping the needle header 36 to avoid becoming stuck and unable to slide within the barrel 22. In this embodiment, the gas reservoir 46 and release valves 60 are preferably configured so as to provide a substantially symmetrical upstream biassing pressure against the flotation gasket, thereby aiding the flotation gasket in evenly forcing the needle header 36 upstream to prevent the needle header 36 from becoming stuck and unable to slide within the barrel 22. Accordingly, the invention is not to be limited by the specific embodiments above; the scope of the invention is as defined in the claims.

What is claimed is:

1. A pneumatic safety syringe for reducing the risk of accidental needle stabbing after use, the pneumatic safety syringe comprising
   (a) a barrel having an inner surface, an upstream opening and a downstream needle aperture;
   (b) a plunger mating with said barrel for axial movement within said barrel, said plunger having
      (i) an upstream end, said upstream end of said plunger projecting from said upstream opening of said barrel, and
      (ii) a plunger seal at a downstream end of said plunger within said barrel, said plunger seal slidingly engaging said inner surface of said barrel so as to impede leakage of fluid past said plunger seal;
   (c) a needle header mounted in said barrel downstream of said plunger seal, said needle header being situated within said barrel before injecting a medicament using the syringe, such that said medicament is containable within said barrel downstream of said plunger seal and upstream of said needle header;
   (d) a needle having
      (i) an upstream intake for receiving the medicament into said needle, said upstream intake of said needle being attached to said needle header; and,
      (ii) a downstream tip for releasing the medicament into a patient, said downstream tip of said needle projecting out of said downstream needle aperture of said barrel before use of the syringe,
   (e) a releasable holding means within said barrel, said releasable holding means releasably engaging said needle header and said barrel
      (i) in order to resist axial sliding of said needle header within said barrel,
      (ii) such that said needle header and said upstream intake of said needle are situated within said barrel so that said downstream tip of said needle projects out of said downstream needle aperture of said barrel, and
      (iii) such that said releasable holding means is released when a downstream post-injection force is exerted on said plunger and said plunger seal contacts said needle header, thereby overcoming said releasable holding means, permitting said needle header to slide axially within said barrel, and forcing said needle header downstream; and,
   (f) a gas reservoir within said barrel downstream of said needle header, said gas reservoir
      (i) being ruptured by said needle header when said needle header is forced in a downstream direction after said releasable holding means is released, and
      (ii) releasing a non-toxic compressed gas when ruptured, said non-toxic compressed gas being released and contained within said barrel in order to provide an upstream biassing pressure within said barrel upstream of said gas reservoir, said upstream biassing pressure biassing said needle header to slide upstream;

wherein
   (g) when an injection force is applied to said plunger, said plunger seal imparts a downstream biassing pressure to said medicament contained in said barrel between said plunger seal and said needle header, said downstream biassing pressure of said medicament being sufficient to force said medicament through said upstream intake and injected into a patient via said downstream tip by said plunger, and, said releasable holding means resisting said downstream biassing pressure exerted on said needle header by said medicament as said medicament is forced through said upstream intake;
   (h) after substantially all of the medicament is forced into said needle, said plunger seal seals said needle intake and said downstream post-injection force exerted by said plunger overcomes said releasable holding means, thereby releasing said needle header to slide downstream; and
   (i) when said needle header ruptures said gas reservoir, said upstream biassing pressure of said non-toxic compressed gas biases said needle header to slide upstream within said barrel, thereby effecting withdrawal of said needle within said barrel.

2. A pneumatic safety syringe as defined in claim 1 further comprising a plunger lock for blocking downstream movement of said plunger after retraction of said needle, wherein during retraction of said needle, said compressed gas forces said plunger seal past said plunger lock such that said plunger seal is upstream of said plunger lock, and after retraction said plunger lock impedes said plunger seal from subsequently sliding downstream of said plunger lock, thereby impeding re-extension of said needle through said downstream needle aperture.

3. A pneumatic safety syringe as defined in claim 2 wherein said plunger lock has a shallow downstream side and a steep upstream side such that when said gas reservoir is ruptured, said plunger seal is forced over said shallow downstream side by said biassing pressure of said compressed gas, and when said plunger seal is upstream of said plunger lock, said steep upstream side of said plunger lock blocks subsequent downstream sliding of said plunger.

4. A pneumatic safety syringe as defined in claim 2, further comprising a spike pointing downstream on said plunger seal, whereby after said releasable holding means has been released by said plunger, and said needle header is being forced axially downstream by said plunger, said spike penetrates said gas reservoir, thereby rupturing said gas reservoir and releasing said compressed gas.

5. A pneumatic safety syringe as defined in claim 4 wherein said gas reservoir comprises a release valve aligned with said spike, such that said spike penetrates said release valve when said needle header is forced axially downstream by said plunger, thereby rupturing said gas reservoir and releasing said compressed gas.

6. A pneumatic safety syringe as defined in claim 5 further comprising a flotation gasket mounted for axial sliding within said barrel and situated downstream of said needle header within said barrel, said flotation gasket being symmetrically configured about the central axis of said barrel so as to evenly force said needle header upstream, thereby reducing the risk of said needle header becoming stuck and unable to slide within said barrel before said needle is fully retracted, wherein said spike can project through said flotation gasket to rupture said gas reservoir when said downstream post-injection force is applied to said plunger.

7. A pneumatic safety syringe as defined in claim 6 wherein said release valve is situated such that said biassing pressure exerted by said compressed gas within said barrel is symmetrical about the central axis of said barrel, thereby reducing the risk that said needle header will become stuck and unable to slide within said barrel.

8. A pneumatic safety syringe as defined in claim 6 wherein said releasable holding means comprises an o-ring gasket, said inner surface of said barrel having an outer concave recess and said needle header having a circular edge with an inner concave recess, said inner concave recess and said outer concave recess being aligned to define a generally ring-shaped hollow before use of the syringe, said o-ring being located in said generally ring-shaped hollow and impeding axial sliding of said needle header within said barrel by resisting dis-alignment of said inner concave recess and said outer concave recess.

9. A pneumatic safety syringe as defined in claim 8 further comprising a needle membrane for impeding leakage of said compressed gas through said downstream needle aperture.

10. A pneumatic safety syringe as defined in claim 9 wherein said downstream needle aperture comprises a self-sealing means for impeding said needle from being re-extended through said downstream needle aperture after said needle has been retracted into said barrel.

11. A pneumatic safety syringe as defined in claim 10 wherein said self-sealing means comprises a sealing membrane, said sealing membrane being tapered at an angle where said sealing membrane contacts said needle at said downstream needle aperture, such that said sealing membrane permits said needle to be retracted into said barrel, and, when said needle is retracted past said sealing membrane, said sealing membrane collapses to cover said downstream needle aperture.

12. A pneumatic safety syringe as defined in claim 1 wherein after all of said medicament is forced into said needle, said plunger seals said needle intake by covering said needle intake.

* * * * *